United States Patent [19]

Douglass

[11] 4,049,665
[45] Sept. 20, 1977

[54] UNSYMMETRICAL DISULFIDES AS ANTIMICROBIAL AGENTS

[75] Inventor: Miriam Lois Douglass, Piscataway, N.J.

[73] Assignee: Colgate-Palmolive Company, New York, N.Y.

[21] Appl. No.: 644,261

[22] Filed: Dec. 24, 1975

[51] Int. Cl.² .......................................... C07D 213/04
[52] U.S. Cl. ...................... 260/294.8 J; 260/294.8 G; 252/106; 252/107; 424/263; 424/DIG. 4
[58] Field of Search .................. 260/294.8 J, 294.8 G; 424/263, DIG. 4; 252/106, 107

[56] References Cited

U.S. PATENT DOCUMENTS 2,922,790  1/1960  Rockett et al. ................ 260/294.8 J
3,966,928  6/1976  Douglass .............................. 252/106

OTHER PUBLICATIONS

The Naming and Indexing of Chemical Compounds vol. 56 (1962) p. 89n.
Runge et al., Chem. Abstracts, vol. 53, (18), 17118-i--17,119d, Sept. 25, 1959.

*Primary Examiner*—Alan L. Rotman
*Attorney, Agent, or Firm*—Richard N. Miller; Murray M. Grill; Herbert S. Sylvester

[57] ABSTRACT

Novel unsymmetrical disulfides of pyridine-1-oxide and acid addition salts thereof, having particular utility as antimicrobial agents per se and in skin cleansing detergent compositions, shampoos, hair dressings, disinfectants, preservatives and the like.

6 Claims, No Drawings

UNSYMMETRICAL DISULFIDES AS ANTIMICROBIAL AGENTS

This invention relates to unsymmetrical disulfides containing one 1-oxo-2-pyridyl radical having both antibacterial and antifungal activity, methods of manufacturing these compounds and compositions containing them.

The art is replete with antibacterial agents and varied compositions containing such agents. Symmetrical and unsymmetrical sulfides of pyridine-1-oxide, salts thereof, and symmetrical disulfides thereof, are known to possess antibacterial and antifungal activity. In addition, trichloromethyl disulfide of pyridine-1-oxide is disclosed in U.S. Pat. No. 2,922,790 to possess pesticidal properties desirable in soil and foliage fungicides (agricultural pesticide). The -CCl$_3$ radical is in all probability responsible for the pesticidal activity of the pyridine-1-oxide trichloromethyl disulfide. However, unsymmetrical disulfides containing one 1-oxo-2-pyridyl radical and one unsubstituted alkyl or alkenyl radical or an aryl or aralkyl radical which may contain substituents such as halo, alkyl, or alkoxy, are not disclosed in the prior art. It has now been found that the instant novel compounds possess the property of wide-spectrum and superior antibacterial and antifungal activity per se as well as when incorporated into compositions such as preservatives, disinfectants, skin cleansing detergents, shampoos, hair dressings, and the like.

A particularly difficult medium for successful employment of an antimicrobial compound is the human scalp and the hair thereon. Due to continued secretions of sebum and perspiration and deposits of dust, grease and oils on the scalp, often in part at least attributable to the use of preparations for treating the scalp and hair, particularly favorable conditions for the growth of microorganisms often prevail on the scalp. Even if the hair and scalp are washed fairly frequently, growth of microorganisms is generally faster than on most other parts of the human body and consequently the actions of antimicrobial compounds employed thereon are often ineffective. However, by the use of the compounds of this invention, good activity is obtained against microorganisms commonly found on the scalp and frequently associated with the dandruff syndrome.

The present compounds may be used in solutions, emulsions or suspensions, or as solids. They are usually in the form of aqueous solutions or suspensions and may be applied to sites on which growth of microorganisms is to be counteracted. For ease of application to such sites, they may be included in various carrier compositions and are considered to be especially useful in hair-dressing preparations and in shampoos.

In accordance with the present invention, there are provided novel unsymmetrical disulfides containing one 1-oxo-2-pyridyl radical having the following structural formula:

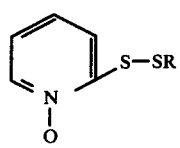

I.

wherein R is selected from the group consisting of straight and branched chain C$_1$–C$_{12}$ alkyl, C$_3$–C$_{12}$ alkenyl, aryl and aralkyl groups, wherein the aromatic ring may be carbocyclic or heterocyclic and may be substituted by halo, C$_1$–C$_6$ alkyl or alkoxy groups; and acid addition salts thereof. The carbocyclic compounds include the phenyl and naphthyl radicals and the heterocyclic compounds include the furyl, thienyl and pyridyl radicals. The alkenyl radical must contain at least three carbon atoms in order to avoid the proximity of an unsaturated carbon to the sulfur atom, which would yield an unstable compound.

Salts of instant unsymmetrical disulfides have the formula:

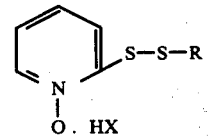

II.

wherein R has the same meaning as is Formula I, X is any suitable anion such as halide, sulfate, nitrate, acetate, and the like.

Specific examples include:
4-Chlorophenyl 1-oxo-2-pyridyl disulfide,
Phenyl 1-oxo-2-pyridyl disulfide,
Benzyl 1-oxo-2 pyridyl disulfide,
2,4-Dichlorobenzyl 1-oxo-2-pyridyl disulfide,
3,4-Dichlorophenyl 1-oxo-2-pyridyl disulfide,
4-pyridyl 1-oxo-2-pyridyl disulfide,
4-Chlorobenzyl 1-oxo-2-pyridyl disulfide,
3-pyridyl 1-oxo-2-pyridyl disulfide,
3,4-Dichlorobenzyl 1-oxo-2-pyridyl disulfide,
2,5-Dichlorophenyl 1-oxo-2-pyridyl disulfide,
p-Methoxyphenyl 1-oxo-2-pyridyl disulfide,
Hexyl 1-oxo-2-pyridyl disulfide,
Methyl 1-oxo-2-pyridyl disulfide,
Dodecyl 1-oxo-2-pyridyl disulfide,
3-Thienyl 1-oxo-2-pyridyl disulfide,
Furfuryl 1-oxo-2-pyridyl disulfide,
Decenyl 1-oxo-2-pyridyl disulfide,
Propyl 1-oxo-2-pyridyl disulfide,
Hexenyl 1-oxo-2-pyridyl disulfide,
Iso-propyl 1-oxo-2-pyridyl disulfide,
Allyl 1-oxo-2-pyridyl disulfide,
1-But-2-enyl 1-oxo-2-pyridyl disulfide,
1-But-3-enyl 1-oxo-2-pyridyl disulfide,
and the hydrochloride salts thereof, the hydrobromide salts thereof, the hydrosulfate salts thereof, etc.

These unsymmetrical disulfides of pyridine-1-oxide are generally prepared by reacting mercaptopyridine-1-oxide or the sodium salt thereof with a sulfenyl halide containing the R radical at temperatures not to exceed 30° C, and preferably at 10°–30° C for a period of about ¼ to 1 hour with continuous agitation. When the R radical is an alkyl or alkenyl, temperatures below 20° C are preferred because of the heat instability of the sulfenyl halide. The reaction proceeds in accordance with the following equation:

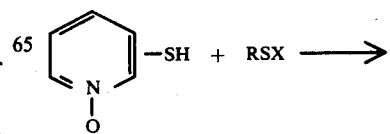

1.

-continued

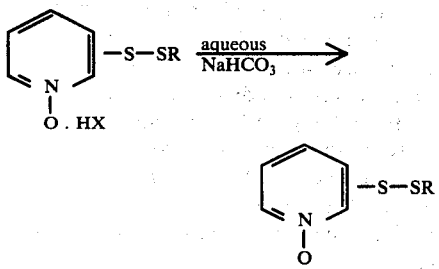

wherein R has the same meaning as above and X is a halide ion. The reaction is preferably conducted under anhydrous conditions and in the presence of a hydrocarbon solvent such as benzene, anhydrous diethyl ether and the like. The hydrohalide salt is collected by filtration and is subsequently neutralized with an aqueous solution of sodium bicarbonate or other suitable base. The resultant disulfide is water-insoluble and can readily be collected by filtration.

The sulfenyl halide may be prepared in situ and is preferably prepared from the corresponding thiol by reacting with N-bromo or N-chloroimides in the presence of a suitable hydrocarbon solvent at room temperature, and preferably at 10°–30° C for a period of 15 minutes to an hour with continuous agitation. This method is described in Chem. Abstracts, 46, 529i (1952). This reaction proceeds in accordance with the following equation:

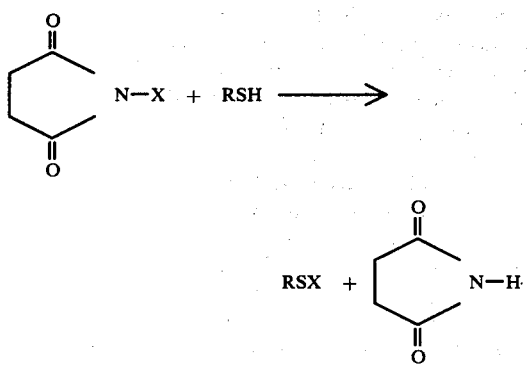

The imide by-product is insoluble in the hydrocarbon solvent utilized in this reaction and can easily be separated by filtration from the solution containing the sulfenyl halide.

The sulfenyl halide may be prepared by any other known process including the halogenation of the corresponding disulfide or corresponding thiol. These methods are not as desirable because of possible side reactions, such as halogenation of the aromatic nucleus or the aliphatic chain; oxidation beyond the sulfenyl halide stage, etc.

The unsymmetrical disulfides of the instant invention may also be prepared by other methods under suitable conditions. For example, mercaptopyridine-1-oxide may be reacted with sulfenamides or thiol-sulfonates. However, side reactions occur during these reactions inclusive of the formation of symmetrical disulfides, thereby giving poor yields of the unsymmetrical disulfide.

More specifically, the unsymmetrical disulfides of pyridine-1-oxide of the instant invention are prepared from known starting materials. 4-Chlorobenzenesulfenyl chloride may be prepared by reacting at room temperature and preferably at 10°–30° C equimolecular amounts of 4-chlorobenzenethiol and N-chlorosuccinimide in dry benzene. After agitating for twenty minutes, the orange benzene solution containing the sulfenyl chloride is decanted from the succinimide and the solution is cooled. Other known processes of obtaining the sulfenyl chloride may be utilized. Equimolecular amounts of mercapto-pyridine-1-oxide dissolved in anhydrous ether is reacted at room temperature and preferably at 10°–30° C, with the benzene solution of 4-chlorobenzenesulfenyl chloride to give a 77% yield of the disulfide hydrochloride which is collected by filtration. A saturated aqueous solution of sodium bicarbonate is added to a stirred suspension of the hydrochloride in water until a pH of 8 is obtained. A quantitative yield of 4-chlorophenyl 1-oxo-2-pyridyl disulfide is collected by filtration and recrystallized from acetone and has a melting point of 133.5°–137.5° C.

For clarity of presentation, the above description of methods of making the invented compounds has been given with respect to a particular starting material and corresponding derivatives thereof. However, it must be realized that such methods are also applicable to reactions utilizing different starting materials and effected by different reagents, which are equivalent in their activities to those described. Thus, instead of utilizing 4-chlorobenzenethiol as the starting material, branched- or straight-chain $C_1$–$C_{12}$ alkyl or $C_3$–$C_{12}$ alkenyl mercaptans or other aryl or aralkyl mercaptans in which the aromatic ring may be carbocyclic or heterocyclic and contain the substituents halo, $C_1$–$C_6$ alkyl or alkoxy, may also be employed as the starting material. The solvents to be employed will be such as are conducive to dissolving the reagents and which are unaffected by the reaction.

The acid salt of the unsymmetrical disulfide of pyridine-1-oxide may be converted to the corresponding disulfide by treatment with any suitable base for removing the acid radical. Thus, usually an aqueous solution of sodium bicarbonate may be used to recover the unsymmetrical disulfide of pyridine-1-oxide compound by filtration. The quantity of base utilized is sufficient to obtain a pH in excess of 7, and preferably about a pH of 8.

The disulfide compounds produced exhibit exceptionally good antimicrobial properties. They are found to have wide-spectrum antibacterial activity and to be effective in killing bacteria and in limiting the growths of a variety of organisms. Particularly, they are very effective against the organism *Pityrosporum ovale,* commonly found in the scalp and frequently associated with the dandruff syndrome. Often it is difficult to have a broad spectrum antimicrobial compound be effective against *P. ovale.* In addition to the excellent utilities of the present compounds against such microorganisms, it is found that these compounds are compatible with a wide variety of compositions and media in which they are employed. Thus, aqueous and alcoholic solutions of these compounds are useful, as are cosmetic preparations containing them, whether based on aqueous or lipophilic media or combination of both such phases. For example, the present antimicrobial compounds may be used in cosmetics or detergents, including liquid, solid, and semi-solid paste, cream or gelatinous preparations. They may be employed in soaps, shampoos, hairdressings, dusting powders or talcs, foot powders, aerosol spray preparations of various types, antiperspirants, deodorants, antiseptics and many other materials intended for cleaning, grooming or sanitizing purposes. Perhaps the most preferred compositions containing these compounds are those which are used in contact with the human hair or scalp, where the microorganism *P. ovale* is usually present, such as shampoos and hairdressings. Water- or alcohol-soluble active ingredients are necessary for the formulation of transparent antidandruff hair products. The solubility at pH-7 of the acid salts of instant unsymmetrical disulfides render them suitable for hairdressings. The disulfides per se are insoluble and thus amenable to formulation only in opaque products. After use of such preparations, it appears that the effects of the present antimicrobial compounds are long lasting.

The unsymmetrical disulfides of instant invention are effective against such potent gram-positive organisms as *Staphylococcus aureus* and *Streptococcus mitis*, gram negative bacteria such as *Escherichia coli* and *Pseudomonas aeruginosa*, as well as against the yeasts as *Candidia albicans* and *Pityrosporum ovale* and the molds *Trichophyton mentagrophytes* and *Aspergillus niger*.

The following Table I clearly shows that the unsymmetrical disulfides of instant invention are more active against bacteria and fungi and more toxic toward *Pityrosporum ovale*, the yeast associated with the dandruff syndrome, than the symmetrical disulfide of mercaptopyridine-1-oxide.

TABLE II

Antimicrobial Activity of Sulfides 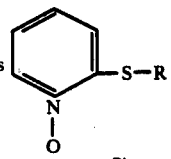

| R | *Pityrosporum ovale* |
|---|---|
| 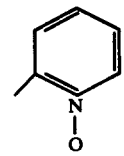 | 500 |
| 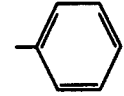 | >50 |
|  | 500 |
| 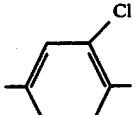 | 500 |
| 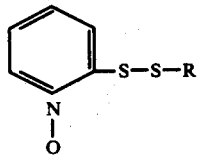 | 500 |

TABLE I

Antimicrobial Activity* of Disulfides

| R | Gram Positive | | Gram Negative | | Yeast | | Mold | |
|---|---|---|---|---|---|---|---|---|
| | S. aureus | Str. mitis | E. coli | Ps. aeruginosa | C. albicans | P. ovale | T. mentagrophytes | A. niger |
| (phenyl-N-oxide) | 7.8 | 31.2 | 62.5 | 250 | 31.2 | 6.25–31.2 | 0.5 | 62.5 |
| (phenyl) | 3.9 | 15.6 | 31.2 | 250 | >1000 | 0.1 | 15.6 | 15.6 |
| —CH₂—(dichlorophenyl) | <0.5 | 7.8 | 31.2 | 125 | 7.8 | 0.5–3.9 | <0.5 | 15.6 |
| (chlorophenyl) | | | | | | 3.9 | | |
| (dichlorophenyl) | | | | | | 15.6 | | |
| —CH₂—(chlorophenyl) | | | | | | 1.9 | | |
| —CH₂—(chlorophenyl) | | | | | | 3.9 | | |

*Data indicates minimum inhibitory concentration in parts per million tested by the two-fold serial dilution text method utilizing 1% solution of the test material in 95% ethyl alcohol.

None of the unsymmetrical or symmetrical sulfides of mercaptopyridine-1-oxide are active towards *Pityrosporum ovale* as shown in Table II.

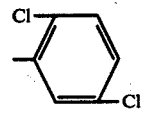

TABLE II-continued

Antimicrobial Activity of Sulfides

| R | Pityrosporum ovale |
|---|---|
| —CH$_2$—C$_6$H$_5$ | >50 |
| —CH$_2$—C$_6$H$_4$Cl | >500 |
| —CH$_2$—C$_6$H$_3$Cl$_2$ | >500 |
| —CH$_2$—C$_6$H$_3$Cl$_2$ (isomer) | 500 |
| —CH$_2$—(furyl) | 500 |
| —CH$_3$ | 500 |
| —CH$_2$CH=CH$_2$ | 500 |
| —(CH$_2$)$_5$CH$_3$ | >50 |
| —(CH$_2$)$_{11}$CH$_3$ | >50 |
| —CH$_2$CO$_2$H | >50 |

A high level of activity against the yeast most frequently associated with dandruff, *Pityrosporum ovale*, is exhibited by the compounds of instant invention. Such effects of these compositions have not been noted before and the active antimicrobial compounds and compositions containing them have not been taught or suggested by the prior art.

In addition to the new compounds and methods for their manufacture, also within the present invention are cosmetic and detergent compositions containing such compounds as active wide-spectrum antimicrobial ingredients, and antimicrobial uses of the compounds and such compositions. It is considered that the present antimicrobials are useful in a wide variety of cosmetic preparations, including hairdressings, hair tonics, hair waving solutions, hair dyes, bleaches, rinses, face creams, face powders, foot powders, body lotions, tanning agents, antiperspirants, sunscreens, personal deodorants, make-up preparations, bath oils, facial treatments, astringents, shaving creams, aftershave lotions and various other preparations for treatment of the hair or skin, in which antibacterial or antifungal activity is useful. Among the detergent compositions which can usefully include the present antimicrobial compounds are bar soaps, liquid soaps, soap shampoos, synthetic detergent shampoos, heavy duty synthetic organic detergents, inorganic detergent salts, pre-soak compositions, which may include enzymes, softeners, dishwashing products, synthetic detergents intended for washing hard surfaces, e.g., janitorial detergents, floor cleaning compositions and other detergent-related products such as wax-removers, organic solvent solutions of surface active materials, compositions for employment with steam cleaning machinery, car washes, and sterilizing preparations.

The cosmetic compositions may contain from 0.1 to 99% of active ingredients for the primary purpose for which they are intended, together with from 0.1 to 10%, preferably from 0.1 to 3%, of a compound of the present invention. Usually the cosmetic vehicle will contain from 1 to 100% of an aqueous or an oily phase or a solid material (foot and face powders), and sometimes, as in the case of emulsions, will contain both aqueous and oily phases, often with a surface active material to aid in emulsification. Such surface-active agents may be anionic, nonionic, cationic or amphoteric and are usually present in emulsified cosmetics in proportions of from 0.5 to 20% thereof, preferably 0.5 to 10%.

Although the most preferred embodiments of the invention, hairdressings or other preparations intended for application to the hair, may be essentially lipophilic, essentially hydrophilic or emulsions, and may even be inert powders, the present compounds may be employed in any such medium. If the medium is lipophilic, there will usually be present from 50 to 99% of oil, such as mineral oil, lanolin, lanolin derivatives or other lipophilic materials, together with one or more of the present compounds. A solvent, e.g., a lower alkanol such as ethanol or isopropanol, may also be used to thin the lipophilic phase to make it easier to apply. It will usually be from 5 to 80% of the cosmetic. If the preparation is hydrophilic, it will usually contain from 50 to 99% of water, sometimes with 5 to 40% lower alkanol solvent associated therewith, plus one or more of the present antimicrobial compounds. The emulsions may have from 1 to 99%, usually from 20 to 80%, of either lipophilic or hydrophilic materials, with essentially the balance thereof being of the other type. The various active ingredients utilized to give the different cosmetic preparations their desired properties are well known and are exhaustively described in the text by Edward Sagarin, Cosmetics Science and Technology (1957), and therefore will not be listed here. However, for example, it is mentioned that with respect to hairdressings, ordinarily a mineral oil and lanolin will be employed to condition the hair and facilitate its taking of waving and combing.

In the case of hair grooming compositions, the vehicle will include a nonvolatile organic hair grooming agent to facilitate grooming of the hair and scalp and to keep the hair in place. Examples of such agents include castor oil, mineral oil, lipophilic lower alkoxypolypropylene glycols having a molecular weight in the range of 1,000 to 2,500, such as butoxy polyoxypropylene glycols having a molecular weight of about 1,700; hydrophobic mixed polyethylene polyalkylene (C$_3$–C$_4$) glycol condensates on butanol having a molecular weight of about 400 to 4,000 and containing from 35 to 65 percent by weight of polyethylene glycol, such as Ucon 50 HB 660; polyhydric alcohols containing 2 to 3 carbon atoms such as glycerol and propylene glycol; and gums, such as gum tragacanth. It is preferred to employ those substantially nonvolatile organic grooming agents which have a molecular weight of above 75, and preferably above 200, and which contain an alcoholic hydroxy group, such as the aforementioned glycols, polyhydric alcohols, polymerized alkylene oxides, and castor oil.

The concentration of the nonvolatile, organic hairgrooming agent in the hair grooming compositions will range from 0.5 to 65 percent, preferably from 3 to 50 percent by weight of the composition. The balance of the vehicle will vary according to the form of the resultant product, and generally will be an aqueous medium, such as water or mixtures of water and a low monohydric alcohol, such as ethanol or isopropanol. In the aqueous alcoholic mixtures, as little as 5 percent by weight of water may be present, with the balance being lower alcohol. Single-phase compositions may include about 30 percent to 80 percent by weight of water; whereas emulsion compositions generally will be free of alcohol.

The cosmetic compositions for the hair and skin may also contain as adjuvant materials various substances, such as vitamins, lanolin, bacteriocides, plant extracts, coloring agents, perfumes, thicheners such as cellulose, opacifiers, and sequestering agents in order to enhance the cosmetic or antimicrobial properties of the resultant compositions. Buffers may also be included to provide a pH of 5 to 10, and preferably above about 7.0.

Antiperspirants will normally contain an active chemical for such purpose, such as aluminum chlorhydrate. Dusting powders will normally be based on talc, silica, or other special form of such materials, such as pyrogenic silica. Skin creams or lotions will usually include stearic acid or other cold cream ingredients. The proportions of such active materials as was previously mentioned, may be varied widely, as is known in the art, and may constitute from 0.1 to 99% by weight of the total composition.

The detergent compositions in which the present anti-microbial compounds are useful may be either built or unbuilt products and may be based on anionic, cationic, nonionic and/or amphoteric surface-active compounds. These are well known and are described in the text by Schwartz, Perry and Berch, Surface Active Agents and Detergents, Volume II, (1958), particularly at pages 321 and 621-625. Most frequently, the detergents employed will be anionic detergents, including the common higher fatty acid soaps of alkali metals and the synthetic anionic detergent salts such as those which are currently commercially used.

As examples of the anionic synthetic organic detergents, there may be mentioned the $C_{10}$–$C_{20}$ alkane sulfonates, $C_8$–$C_{18}$ fatty acid monoglyceride sulfates, linear $C_{10}$–$C_{15}$ alkyl benzene sulfonates, $C_8$–$C_{18}$ fatty acid soaps, $C_{10}$–$C_{15}$ alkyl polyoxyethylene, (1–5EO) sulfates, and hydroxyalkylene ($C_8$–$C_{18}$) sulfonates containing 1–5 hydroxy groups, $C_8$–$C_{18}$ alcohol sulfates, salts of $C_1$–$C_3$ alcohol esters of $C_8$–$C_{18}$ sulfofatty acids, $C_8$–$C_{12}$ alkyl phenol polythoxy ether sulfates, $C_8$–$C_{18}$ acyl sarcosinates, $C_8$–$C_{18}$ acyl esters of isethionates, and $C_8$–$C_{18}$ acyl N-methyl taurides, to name only a few. The salt forming metals or other suitable salt-forming radicals for the detergents are preferably alkali metal, such as potassium or sodium, but alkaline earth metals such as calcium and magnesium, and ammonium, alkylamine, and alkanolamine salts may also be used. Some specific examples of these detergents are sodium lauryl sulfate; sodium linear tridecyl benzene sulfonate, triethanolamine lauryl sulfate; sodium or potassium coconut oil-tallow soaps; sodium lauryl sulfonate; potassium hexadecylnaphthalene sulfonate; lauryl alcohol ethylene oxide sulfate comprising four ethoxy groups per molecule; potassium stearyl glyceryl ether sulfonate; sodium lauroyl sarcosinate; and magnesium methyl tauride.

Among the nonionic surface-active agents are the condensation products of $C_8$–$C_{12}$ alkylated phenols with ethylene oxide, $C_8$–$C_{18}$ fatty alcohols with ethylene oxide and polypropylene glycols or other polyols with ethylene oxide, wherein from 5 to 30 moles of ethylene oxide are associated with the hydrophobic moiety.

The polar nonionic detergents are those in which the hydrophilic group contains a semi-polar bond directly between two atoms, for example, N→O, P→O, As→O, and S→O. There is charge separation between the two directly bonded atoms, but the detergent molecule bears no net charge and does not dissociate into ions.

The polar nonionic detergents of this invention include open-chain aliphatic amine oxides of the general formula $R_1R_2R_3N\rightarrow O$. For the purposes of this invention, $R_1$ is an alkyl, alkenyl, or monohydroxyalkyl radical having about 10 to 16 carbon atoms, $R_2$ and $R_3$ are each selected from the group consisting of methyl, ethyl, propyl, ethanol, and propanol radicals.

Other operable polar nonionic detergents are the open-chain aliphatic phosphine oxides having the general formula $R_1R_2R_3P\rightarrow O$, wherein $R_1$ is an alkyl, alkenyl, or monohydroxyalkyl radical ranging in chain length from 10 to 18 carbon atoms, and $R_2$ and $R_3$ are each alkyl and monohydroxyalkyl radicals containing from 1 to 3 carbon atoms.

Among the cationic surface-active materials are N-2-amino-ethyl-higher alkyl amines; N-2-aminoethyl higher fatty acid amides; and quaternary ammonium compounds wherein an alkyl group is of 12 to 18 carbon atoms and other groups attached to the nitrogen are alkyls of 1 to 3 carbon atoms. Among such are ethyldimethylstearyl ammonium chloride; benzyl dimethylstearyl ammonium chloride; and trimethylcetyl ammonium bromide.

The amphoteric detergents, useful herein, are generally water-soluble salts of derivatives of aliphatic amines which contain at least one cationic group which may be part of a heterocyclic ring, and an anionic water-solubilizing carboxyl, sulfo, sulfato, phosphato or phosphoro group in their molecular structure. Examples of suitable amphoteric detergents include the $C_8$–$C_{18}$ alkyl beta-aminopropionates, RN(H)$C_2H_4$COOM; the $C_8$–$C_{18}$ alkyl beta-iminodipropionates, RN($C_2H_4$COOM)$_2$; the $C_8$–$C_{18}$ alkyl and hydroxy alkyl taurinates, RN(CH$_3$)$C_2H_4$SO$_3$M; and long chain ($C_7$–$C_{17}$) imidazole derivatives having the following formulas:

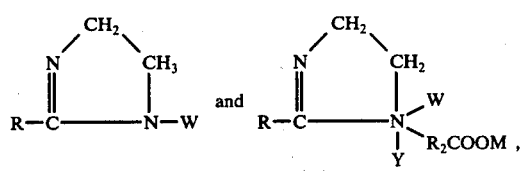

wherein W is selected from the group of

ROH, $R_2$COOM, and $R_2$ O$R_2$COOM,

Y is selected from the group containing OH$^-$, $R_3$OSO$_3^-$; $R^2$ is an alkylene or hydroxyalkylene group containing 1 to 4 carbon atoms; and M is a water-soluble cation such as sodium, potassium, ammonium or alkylol ammonium. Preferred detergents are sodium N-lauryl beta-amino-propionate, disodium N-lauryliminodipropionate, and the disodium salt of 2-lauryl-cyclomidium-1-hydroxyl, 1-ethoxy-ethanoic acid, 1-ethanoic acid.

Zwitterionic detergents such as the betaines and sulfo-betaines having the following formula are also useful:

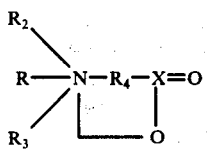

wherein R is an alkyl group containing about 10 to 18 carbon atoms, $R_2$ and $R_3$ are each $C_1$-$C_3$ alkyl, $R_4$ is an alkylene or hydroxyalkylene group containing about 1 to 4 carbon atoms, and X is C or S:O. The alkyl group can contain one or more intermediate linkages such as amido, ether or polyether linkages, or non-functional substituents such as hydroxyl or halogen which do not substantially affect the hydrophobic character of the group. When X is C, the detergent is called a betaine; and when X is S:O, the detergent is called a sulfobetaine or sultaine. Preferred betaine and sulfobetaines are 1-(lauryldimethylammonio) acetate, 1-(myristyldimethylammonio) propane-3-sulfonate, and 1-(myristyldimethylammonio)-2-hydroxy-propane-3-sulfonate.

In the built detergents, water-soluble inorganic salt builders or organic builders are present to assist in dispersing peptizing, sequestering, and alkalizing, whereby detergency is increased. Among these are the pyrophosphates, tripolyphosphates, silicates, borates, carbonates, sesquisilicates and other water-soluble alkaline salts, for which the salt-forming metal is usually an alkali metal, such as sodium or potassium.

Generally, in the detergent compositions, the proportion of detergent will be from 5 to 99% by weight, and preferably there will be present from 10 to 50% thereof in both built and unbuilt compositions. The builder salts, when present, will normally be from 15 to 60% by weight of the composition, and the active antimicrobial compound will be from 0.1 to 10% thereof, preferably from 0.1 to 5% thereof, and most often will be from 0.5 to 3% of the total product. Such compositions will usually include an adjuvant or mixture thereof in an amount from 0.1 to 25% by weight. Such adjuvants include perfumes, dyes, bleaches, softening agents, antiredeposition agents, emollients and brighteners. In the preferred detergents, which are essentially unbuilt shampoo preparations, there will be present from 5 to 40% of soap or synthetic organic detergent or mixture thereof, from 0.1 to 5% of antimicrobial compounds, and from 1 to 20% of various adjuvants such as thickeners, foaming agents, perfumes, coloring materials, and conditioning agents. The balance will be an aqueous medium such as water, or a mixture of water with 5 to 25% by weight of a $C_1$-$C_3$ alkanol, if desired.

The present antimicrobial preparations, cosmetics, or detergents, are used in accordance with normal techniques. Thus, to sterilizze or make antibacterial a particular surface, a suitable solution of the present unsymmetrical disulfide of pyridine-1-oxide of this invention may be applied to the surface and allowed to remain there, or it may be removed by rinsing after a suitable time. The detergents and cosmetics are used in normal fashion. The unsymmetrical disulfides and the acid salts thereof act to kill bacteria and fungi while on the surface which is a locus thereof. Various of the present compounds are found to be especially useful against bacteria and fungi which normally are resident in the hair, such as *Pityrosporum ovale*.

The following examples are given to illustrate specific preferred embodiments of this invention. Clearly the invention is not limited thereto. All temperatures are given in degrees Centigrade and all parts are by weight, unless otherwise indicated.

EXAMPLE I

Preparation of 4-chlorophenyl 1-oxo-2-pyridyl disulfide

A solution of 2.14 g (0.0148 mole) of 4-chlorobenzenethiol in 15 ml of dry benzene is added to a stirred suspension of 1.98 g (0.0148 mole) of N-chlorosuccinimide in 55 ml of dry benzene at room temperature and continuously agitated. After 20 minutes, the orange solution is decanted from the succinimide. The solution is cooled below 30° C, and to the cooled solution which contains 4-chlorobenzenesulfenyl chloride, is added 1.89 g (0.0148 mole) of 2-mercaptopyridine-1-oxide dissolved in 70 ml of anhydrous ether. After 45 minutes of agitation while cooling to a temperature below 30° C, a 77% yield of the disulfide hydrochloride is collected by filtration. Saturated aqueous sodium bicarbonate is added to a stirred suspension of the hydrochloride in water until a pH of 8 is reached. A quantitative yield of 4-chlorophenyl -1-oxo-2-pyridyl disulfide is collected by filtration and recrystallized from acetone. The disulfide has a melting point of 133.5°–137.5° C.

| Elemental Analysis: | C | H | S |
| --- | --- | --- | --- |
| Calculated: | 48.98 | 2.99 | 23.77 |
| Found: | 48.88 | 2.87 | 24.07 |

EXAMPLE II

Preparation of 3,4-Dichlorobenzyl 1-oxo-2-pyridyl disulfide 3,4-Dichlorophenylmethanesulfenyl chloride is prepared from the corresponding 3,4-dichlorobenzyl mercaptan in accordance with the procedure of Example I for the preparation of the sulfenyl chloride, except that this reaction is conducted under cooling conditions. The sulfenyl chloride is reacted with the mercaptopyridine-1-oxide as described in Example I, giving an 84% yield of 3,4-dichlorobenzyl 1-oxo-2-pyridyl disulfide having a melting point of 133.0°–134.0° C and

| Elemental Analysis of: | C | H | N | S |
| --- | --- | --- | --- | --- |
| Calculated: | 45.29 | 2.85 | 4.40 | 20.15 |
| Found: | 44.90 | 2.85 | 4.45 | 20.07 |

EXAMPLE III

Preparation of 2,4-Dichlorobenzyl 1-oxo-2-pyridyl disulfide 2,4-Dichlorobenzyl mercaptan is substituted for the mercaptan of Example II. The method of Example II is used, obtaining an 85% yield of 2,4-dichlorobenzyl 1-oxo-2-pyridyl disulfide having a melting point of 111.0°–112.1° C.

| Elemental Analysis: | C | H | S | Cl |
| --- | --- | --- | --- | --- |
| Calculated: | 45.29 | 2.85 | 20.15 | 22.28 |
| Found: | 45.51 | 2.56 | 20.32 | 22.12 |

EXAMPLE IV

Preparation of 3,4-Dichlorophenyl 1-oxo-2-pyridyl disulfide 3,4-Dichlorobenzenethiol is substituted for the thiol in Example I and the method of Example I is used, giving a 68% yield of 3,4-dichlorophenyl 1-1 -oxo-2-pyridyl disulfide having a melting point of 135.5°–136.7° C.

| Elemental Analysis | C | H | S | Cl |
|---|---|---|---|---|
| Calculated: | 43.43 | 2.32 | 4.61 | 21.08 |
| Found: | 43.29 | 2.30 | 4.06 | 21.22 |

EXAMPLE V

Preparation of Phenyl 1-oxo-2-pyridyl disulfide

Benzenethiol is substituted for the thiol of Example I and the method of Example I is used to obtain a 79% yield of phenyl 1-oxo-2-pyridyl disulfide having a melting point of 82.1°–82.2° C.

| Elemental Analysis: | C | H | N | S |
|---|---|---|---|---|
| Calculated: | 56.14 | 3.85 | 5.95 | 27.25 |
| Found: | 56.50 | 4.11 | 6.17 | 27.00 |

EXAMPLE VI

Preparation of 4-Chlorobenzyl 1-oxo-2-pyridyl disulfide

4-Chlorobenzyl mercaptan is substituted for the thiol in Example II and the procedure of Example II is used to obtain an 89% yield of 4-chlorobenzyl 1-oxo-2-pyridyl disulfide. Melting point 81.5°–84.0° C.

| Elemental Analysis: | C | H | S | Cl |
|---|---|---|---|---|
| Calculated: | 50.79 | 3.55 | 22.60 | 12.49 |
| Found: | 50.89 | 3.50 | 22.78 | 12.83 |

EXAMPLE VII

| Shampoo: | % |
|---|---|
| 4-Chlorophenyl 1-oxo-2-pyridyl disulfide | 1.0 |
| Potassium hexadecyl sulfate | 15.0 |
| Sodium coco-fatty acid monoglyceride sulfate | 15.0 |
| Coconut oil fatty acid diethanolamide | 5.0 |
| Lauric myristic monoethanolamide | 3.0 |
| Perfume | 1.0 |
| Lanolin esters | 1.0 |
| sodium carboxymethyl cellulose | 0.2 |
| Glycerine | 2.0 |
| Water | Balance |

When p-methoxyphenyl 1oxo-2-pyridyl disulfide or hexyl 1-oxo-2-pyridyl disulfide or dodecyl 1-oxo2-pyridyl disulfide or decenyl 1-oxo-2-pyridy disulfide is substituted for 4-chlorphenyl 1-oxo-2-pyridyl disulfide in the foregoing shampoo composition, the resultant shampoo has substantially similar antimicrobial properties. Similarly beneficial results are also obtainable by utilizing other shampoo formulations, based on nonionic or cationic detergents or other of the previously mentioned synthetic detergents instead of the mentioned combination of anionic detergents. A similar result is noted when the shampoo is based on soluble higher fatty acid soap. Usually, for shampoo applications, the milder of the mentioned detergents will be selected so as to avoid unduly drying or embrittling the hair.

EXAMPLE VIII

| Hairdressings: (A) | % |
|---|---|
| Light mineral oil | 72.0 |
| Isopropyl myristate | 22.0 |
| Lanolin | 2.0 |
| Lanolin esters | 1.5 |
| Perfume | 1.2 |
| 3,4-Dichlorobenzyl 2-(1-oxopyridyl) disulfide | 1.3 |
| (B) | |
| Light mineral oil, white deodorized | 45.0 |
| Stearic acid | 5.0 |
| Cetyl alcohol | 2.0 |
| Triethanolamine | 2.5 |
| Perfume | 0.7 |
| Phenyl 2-(1-oxopyridyl) disulfide | 2.0 |
| Water | 42.8 |

Approximately three cubic centimeters per application is used in treating human hair and scalp. This treatment may be repeated daily over a period of weeks. The compositions are especially useful with respect to diminishing fungal and bacterial counts and are particularly effective against *Pityrosporum ovale*, the yeast most frequently associated with dandruff, even in the presence of the sebum normally found on the hair and scalp.

In place of the particular disulfides of the above formulas, similar proportions or variations in proportions, within the ranges described in the specification, may be employed with respect to other unsymmetrical disulfides of instant invention with the obtaining of similar antimicrobial activities. It is noted that the bactericides are especially useful even in the normally oily environment of the scalp and hair and in the lipophilic phases of hairdressings.

Similar results are obtained when the mentioned bactericides are used in similar proportions in other cosmetics, e.g., hair setting compositions, aerosol hair sprays, hair dyes, skin creams, talcum powders and foot powders.

EXAMPLE IX

| Detergent Bar: | % |
|---|---|
| Sodium N lauryl B-iminodipropionate | 8.75 |
| Sodium $C_{10}$–$C_{20}$ alkane sulfonate | 24.25 |
| Sodium tallow soap | 26.40 |
| Sodium Tridecylbenzene sulfonate | 7.30 |
| Syrupy phosphoric acid (85%) | 7.30 |
| Stearic acid | 3.60 |
| Benzyl 1-oxo-2-pyridyl disulfide | 8.10 |
| Water | Balance |
| | 100.0 |

The detergent bar is prepared by admixing an aqueous suspension of benzyl 1-oxo-2-pyridyl disulfide with a mixture of the other ingredients containing about 3 percent moisture, milling on a three-roll mill and plodding at about 110° F to yield a rod for cutting into bars. This bar is effective against P. ovale when used for washing hands.

EXAMPLE X

| Antiperspirant: | % |
| --- | --- |
| Propylene carbonate | 0.06 |
| Perfume | 0.10 |
| Bentone 38[a] | 0.20 |
| Isopropyl palmitate | 1.44 |
| Aluminum chlorohydroxide powder | 3.0 |
| Propellant 12[b] | 23.8 |
| Propellant 11[c] | 70.4 |
| 2,4-Dichlorobenzyl 1-oxo-2-pyridyl disulfide | 1.0 |
| | 100.00 |

[a]Montomorillonite clay,
[b]Dichlorodifluoromethane,
[c]Trichloromonofluoromethane.

EXAMPLE XI

| Cleansing Composition: Ingredients | % |
| --- | --- |
| Sodium tridecyl benzene sulfonate | 9 |
| Sodium lauryl polyethoxamer sulfate | 6 |
| Potassium xylene sulfonate (comm.) | 8.5 |
| Potassium pyrophosphate | 15 |
| 3,4-Dichlorophenyl 1-oxo-2-pyridyl disulfide | 1.0 |
| Water | Balance |

In the above formulation, the higher alkyl benzene sulfonate is a commercial mixture of the propylene tetramer and pentamer benzene sulfonates corresponding on the average to a tridecyl benzene sulfonate. The higher alkyl benzene sulfonate is listed on an active ingredient basis, but contains, in addition, about 1.6 parts of sodium sulfate in the formulation. The polyethoxamer sulfate material has an average of 5 moles ethylene oxide. The inorganic salt builder (pyrophosphate) is listed on an active ingredient basis and is of 90% purity. The xylene sulfonate comprises a mixture of the meta-, para-, and ortho-xylene sulfonates with some toluene sulfonate.

The above composition is a clear solution at room temperature.

EXAMPLE XII

Emollient Cream

| Emollient Cream: Ingredients | % |
| --- | --- |
| Beeswax | 10.0 |
| Spermaceti | 5.0 |
| Light mineral oil | 30.0 |
| Apricot kernel oil | 26.0 |
| Borax | 0.5 |
| Water | 27.4 |
| Perfume | 0.1 |
| 4-chlorobenzyl 1-oxo-2-pyridyl disulfide | 1.0 |

To minimize and retard the development of rancidity, antioxidants may be added to vegetable oils with lower iodine values, or to partially and completely hydrogenated types. Among the more popular antioxidants are propyl gallate, propenyl methyl guaethol, and butylated hydroxyanisole. Methyl and propyl paraben (methyl and propyl p-hydroxy benzoates) are added to the aqueous and oil phases, respectively, as preservatives to minimize or eliminate bacterial contamination. The spermaceti may be reduced or omitted to avoid a waxy feel and to prevent sweating of the hands if used in high concentrations.

The invention has been described with respect to various illustrations and embodiments thereof. However, the invention is broader than the illustrations given and it will be evident to one of ordinary skill in the art that substitutes and equivalents may be employed within the inventive concept. cm What is claimed:

1. An unsymmetrical disulfide compound having the structural formula:

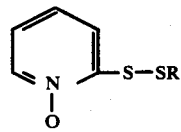

wherein R is a $C_1$-$C_{12}$ alkyl radical, a $C_3$-$C_{12}$ alkenyl radical, a substituted or unsubstituted aryl or aralkyl radical selected from the group consisting of phenyl, benzyl or naphthyl which may be substituted by 1 or 2 halo, $C_1$-$C_6$ alkyl or alkoxy groups, or a heterocyclic radical selected from the class consisting of furyl, thienyl and pyridyl; and acid addition salts thereof selected from the group consisting of halides, sulfates, nitrates and acetates.

2. A compound according to claim 1, wherein R is a halogenated aryl group.

3. A compound according to claim 1, wherein R is a halogenated aralkyl group.

4. A compound in accordance with claim 1, having the following structure:

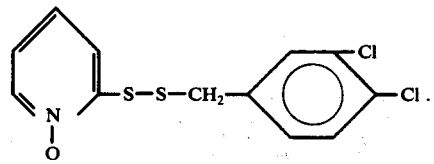

5. A compound in accordance with claim 1, having the following structure:

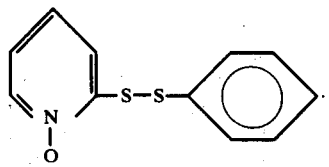

6. A compound in accordance with claim 1, having the following structure:

* * * * *